United States Patent [19]

You

[11] Patent Number: 5,104,322
[45] Date of Patent: Apr. 14, 1992

[54] DENTAL ROOT CANAL SEALER WITH DIMENSION INDICATING CODE

[76] Inventor: Moo C. You, 1018-1, Bangbae-Dong Samik Apt. 1-506, Seocho-Ku, Seoul, Rep. of Korea

[21] Appl. No.: 196,007
[22] Filed: May 19, 1988
[51] Int. Cl.⁵ .............................................. A61C 5/01
[52] U.S. Cl. .................................... 433/224; 433/102
[58] Field of Search ................. 433/80, 102, 141, 215, 433/224, 81

[56] References Cited

U.S. PATENT DOCUMENTS

| | | | |
|---|---|---|---|
| 106,773 | 8/1870 | Blake | 433/102 |
| 171,106 | 12/1875 | Donaldson | 40/913 |
| 1,067,015 | 7/1913 | Fowler | 433/102 |
| 2,915,926 | 12/1959 | Woerner | 40/913 |
| 4,044,468 | 8/1977 | Kahn | 433/102 |
| 4,674,979 | 6/1987 | Jacklich | 433/102 |

OTHER PUBLICATIONS

Hygenic brochure, 1984 The Hygenic Corporation of Ohio.
Silverman's Catalog, 1976, pp. 36-37.
Union Broach Corporation ad, in Dental Survey 7-1979, p. 19.
Pfingst Catalog, 1983, pp. 20-21.

Primary Examiner—John J. Wilson
Attorney, Agent, or Firm—Stanger, Michaelson, Spivak & Wallace

[57] ABSTRACT

A root canal sealer and cleaner provided with a dimension discriminating part at their heads so as to discriminate the dimension easily, and a method and device for forming the dimension discriminating part on the root canal sealer and cleaner.

According to the root canal sealer and cleaner of the invention, a coloring part having a hue for indicating the required dimension is formed directly at the head gripped by an operating tool such as pincers, etc., at the time of the root canal cleaning and sealing treatment of a tooth, so that it is possible to indicate the dimension by each root canal sealer and cleaner itself, to discriminate easily and exactly the dimension of each root canal sealer and cleaner, and to distinguish it from those of different standards even when it is mixed with them in the course of operation. Thereby it is possible to use exactly the root canal sealers and cleaners of required standards, to eliminate various post-treatment impediment factors incidental to use of root canal sealers and cleaners of improper standards, and to carry out a perfect cleaning and tight sealing.

2 Claims, 4 Drawing Sheets

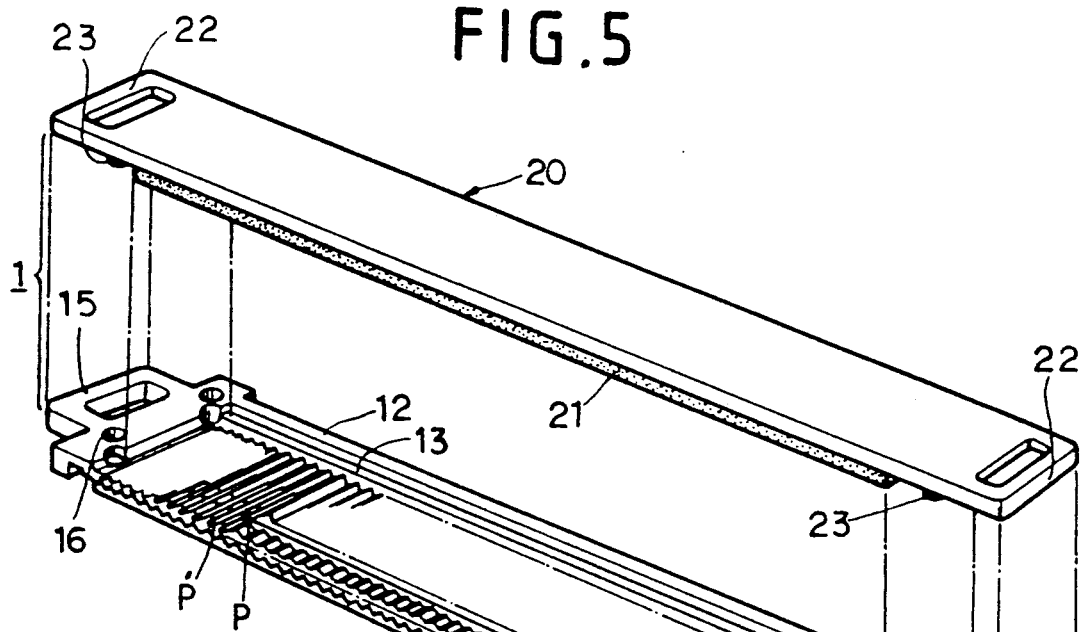
FIG.5
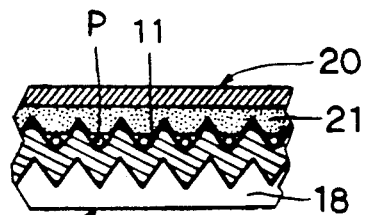
FIG.6A
FIG.6
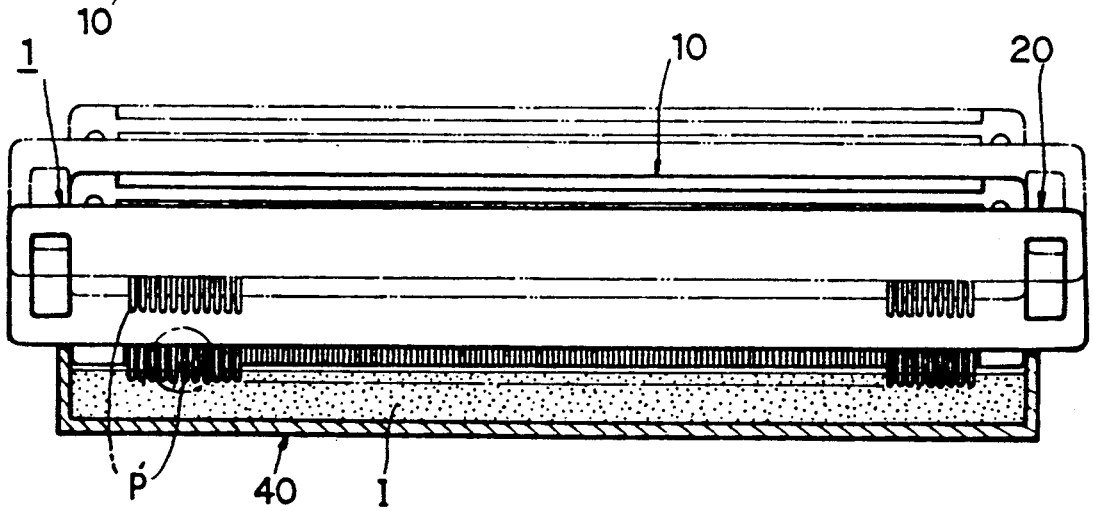

DENTAL ROOT CANAL SEALER WITH DIMENSION INDICATING CODE

BACKGROUND OF THE INVENTION

This invention relates to root canal sealers and cleaners having dimension indications to permit easy identification of their dimensions, and also to a method and means for forming dimension indications on the root canal sealers and cleaners.

When corrosion of a decayed tooth reaches the dental pulp, root canal treatment becomes necessary. This involves removing the nerves and capillary vessels of the tooth, cleaning the hollow neural tube part or root canal of the tooth with a root canal cleaner, and filling the hollow tooth with an air-tight root canal sealer.

Such root canal cleaning and filling is the basis of normal clinical treatment. If the root canal filling is not perfect, a dead cavity may result. The latter may affect the clinical process and ultimately damage the surrounding periodontal tissue and become occasion for the loss of the tooth.

Dental root canal sealers generally use various therapeutic materials such as gum resin, gutta percha points, silver points, or other materials depending upon the purpose and quality of the sealer. Paper points often serve as a cleaning material.

Root canal cleaners and sealers are normally in the form of needles whose front ends are thin and whose diameters increase gradually towards the heads of the opposite sides. Such tapered root canal sealers and cleaners are manufactured in various sizes having front diameters between 0.15 mm and 1.4 mm available in steps of 0.05 mm. Thus, a dentist may select and use the optimal dimensions depending upon the size of the root canal. The length of such root canal sealers and cleaners are standardized at approximately 28 to 30 mm. In general, sealers and cleaners have the same substantial shape. Only the sealer is described by way of illustration of the present invention.

Cleaners may have the same shapes and features as the sealers and may be manufactured in the same manner as the sealers. However, the term sealer is intended to be limited to sealers per se.

Because the difference in the sizes of the dental sealers is so small, it is impossible to discriminate between sealers of different sizes with the naked eye. The manufacturing and packing processes attempt to permit one to discriminate between their sizes by marking the dimension on the boxes containing a prescribed number of root canal sealers. Another method of permitting identification is to attach color coding labels such as red, blue, green, black, white, yellow, etc., labels on such boxes or containers.

However, these methods of dimension indication on a container or box creates problems when root canals sealers having small size differences become mixed up. This makes it possible for one to distinguish them and, if they are misused, they adversely affect the root canal filling and treatment. Hence, misclassification may negatively impact clinical processes after treatment.

SUMMARY OF THE INVENTION

The principal object of the invention is to provide a root canal sealer with a dimension indicator to root canal sealers of different dimension more easily and exactly than with the naked eye.

It is another object of the invention to provide, in forming a dimension discriminating part for indicating the standard on the root canal sealer, a method and device for forming a dimension discriminating part with a selected hue at the head of a root canal sealer using a dental instrument in which a prescribed number of root canal sealer are arranged and held.

According to the present invention, the dimension indicator is formed in a preselected hue at the head of a root canal sealer so that the dimension of the root canal sealer is identified easily by the hue of the dimension indicator.

The dimension discriminating part formed at the head of a root canal sealer can be colored at a time the head of each root canal sealer by passing through a simple coloring process using the body of a dental instrument of simple structure in which a certain number of root canal sealers are arranged and held, and a pressing plate to be covered on the upper part of the body of dental instrument.

BRIEF DESCRIPTION OF THE DRAWINGS

The objects, characteristics and other advantages of the invention appear in the following detailed description of an example, with reference to the accompanying drawings. In the drawings, FIGS. 4 to 6 show a forming process of a dimension discriminating part according to a method of the invention, FIGS. 4(A) and (B) are views illustrating the process to expose and arrange in a specified length the heads of root canal sealers contained in a dental instrument according to the invention, FIG. 5 is a perspective view showing a process to cover a pressing plate for preventing a movement in a state that the head of a root canal sealer is exposed in the front of a dental instrument according to the invention, and FIG. 6 is a view illustrating a process to form a dimension discriminating part by soaking the head of an arranged and fixed root canal sealer in the coloring ink containing in a tray by means of a dental instrument and a pressing plate according to the invention.

DETAILED DESCRIPTION OF THE INVENTION

Figure 1:
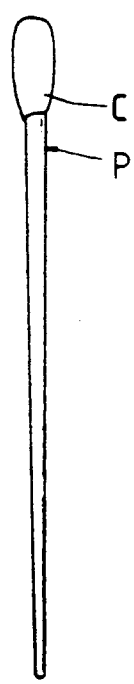
FIG. 1 is a perspective view of a root canal sealer according to the invention.
Figure 2:
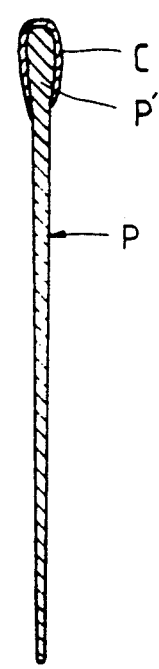
FIG. 2 is a longitudianl sectional view of a root canal sealer shown in FIG. 1.

As shown in FIGS. 1 and 2, which are a perspective view and a longitudinal sectional view of a root canal sealer according to the invention, the root canal sealer P according to the invention comprises a head P' formed at the back end of the body in a needle form tapered slightly through the whole length, and a dimension discriminating or identifying part C in a hue for indicating a selected standard, formed on the surface of the head P'.

Figure 3:
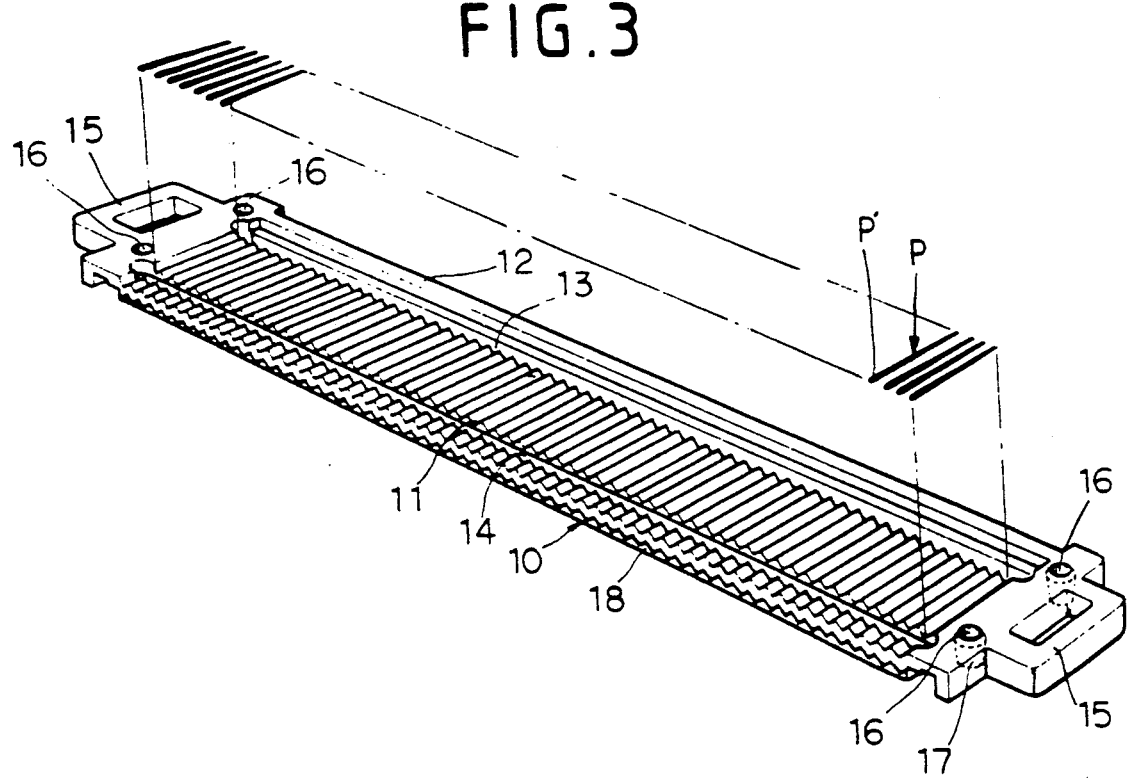
FIG. 3 is a perspective view of a dental instrument according to the invention.

As is shown in FIGS. 3 and 5, the root canal sealer of the invention with a dimension discriminating part C of the hue for indicating the standard is manufactured by making use of a dental instrument 1. The latter includes a dental instrument body 10 in a rectangular plate form having form concave grooves 11 adapted to receive a number of root canal sealers are formed continuously, and a pressing plate 20. The latter covers the upper part of the body 10 and has almost the same width and length as the dental instrument body 10.

Each concave groove 11 formed in said dental instrument body 10 is formed across the direction of the width of the body 10. One end of each concave groove 11 is open to the front side of the body 10, and the opposite end is blocked by an intercepting wall 12 formed along the direction of its length at the rear side of the body 10. Vertical grooves 13 and 14 having prescribed width and depth are formed parallel to each other along the length of the body 10 between the intercepting wall 12 and the rear side of each concave groove 11, and in the inside of the front side of each concave groove 11.

Each end of thus formed dental instrument body 10 is in the form of a knob 15. The upper inside face near the knob contains or handle insert grooves 16 having a give depth at given intervals. Both ends of the bottom of the dental instrument body 10 have downwardly extending insert projections 17 corresponding to the insert grooves 16. The front of the body 10 includes vertical projections 18 corresponding to the vertical grooves 14 on the front.

The bottom of the pressing plate 20 covering the upper part of the dental instrument body 10 supports a pressing member 21 consisting of soft elastic material such as sponge. and the like. As the pressing plate 20 covers the body 10, the pressing member 21 on the bottom presses and fixes the upper face of the root canal sealers P arranged in each concave groove 11 of the body 10, ends of the plate 20 form a handle or knob 22 corresponding to the knob 15 of the body 10. Projections 23 on the bottom of the plate 22 are arranged to enter one or the other insert groove 16 on the body 10.

Figure 4:
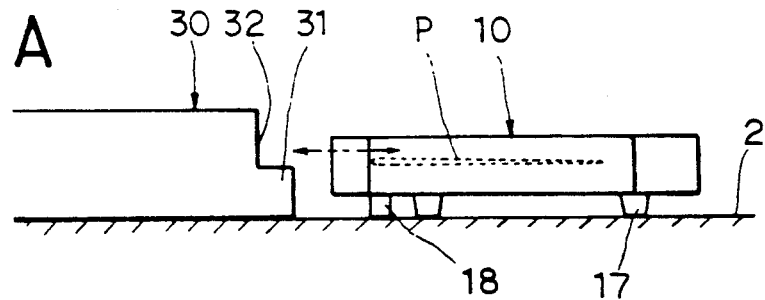
Figure 4:
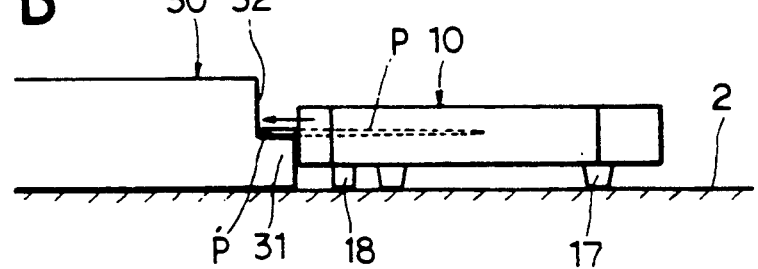

In FIG. 4 a stopper block 30 serves for exposing a specified length of the head P' of each root canal sealer P inserted in each concave groove 11 of said dental instrument body 10. Reference number 32 represents an upper plate of a worktable, and 40 in FIG. 6 represents a tray containing the coloring ink I.

The method to form a coloring part for indicating the dimension of the root canal sealer using the dental instrument of the invention.

In each V-form concave grooves 11 of the dental instrument body 10 according to the invention receives a certain number of root canal sealers P having a standard of the same dimensions. As shown in FIG. 3, the head P' of each root canal sealer P is positioned in the inside of the end of open side of each concave groove 11, so that it is positioned at a prescribed distance in front of the stopper block 30, stepped jaw 31 on the front of the block 30 has a prescribed width and height, that is, a width of about 3 mm and the same height as the bottom of the concave groove 11 of the dental instrument body 10 as shown in FIG. 4(A). As the body 10 of dental instrument is pushed forward slightly, and the front of the dental instrument body 10 contacts the front face of the stepped jaw 31 of the stopper block 30, several times the root canal sealer P inserted in each concave groove 11 projects out toward the front of the dental instrument body 10 by the inertia incidental to an advance of the dental instrument body 10 as shown in (B) of FIG. 4. The head P' contacts a vertical wall 32 of the upper inside of the stepped jaw 31. As shown in FIGS. 5 and 6, the head P' of root canal sealer P inserted in each concave groove 11 is thereby uniformly exposed as much as a prescribed length (a length of about 3 mm equal to the width of the stepped jaw 31) in the front of the dental instrument body 10.

In this state, when the projection 23 on the bottom of the pressing plate 20 is brought in line with the insert groove 16 of the dental instrument body 10 by putting the pressing plate 20 on the upper face of the dental instrument body 10, and at the same time the knobs 15, 22 of both ends in contact with each other are grasped by hands, the pressing member 30 on the bottom of the pressing plate 20 engages the inside of each concave groove 11 and presses and fixes the upper face of the root canal sealers P inserted in the lower side of each concave groove 11 as shown on an enlarged scale in "D" of FIG. 6. This fixes the position of each root canal sealer P so it exposes a prescribed length in the front of the body 10.

The root canal sealer P as shown in FIGS. 1 and 2 is obtained holding the combined dental instrument 1 so that the head P' of each root canal sealer P exposed in the front of the dental instrument body 10 is positioned on the lower side. The process further involves preparing a tray T containing a give quantity of coloring ink I having a prescribed hue, soaking the head P' of root canal sealer P exposed in the front of the dental instrument body 10 in the ink and then taking it out therefrom so that the dimension discriminating part in a required hue is formed at each head P'.

The root canal sealer P of the invention indicates the dimension of each root canal sealer P by forming a color portion C having a hue required for indicating the dimension directly at the head P' of the sealer P to be gripped by an operating tool such as pincers, etc., during root canal sealing treatment of a tooth. This makes it possible to determine easily and exactly the dimension of each root canal sealer P, and to distinguish it easily even if it is mixed with those of different dimensions in the course of handling and operation of the root canal sealers P. Accordingly at allows one to use exactly the root canal sealers of required size. Therefore, it is also possible to eliminate all the post-treatment impeditive factors incidental to a use of the root canal sealers of improper dimensions, and to carry out a perfect and tight sealing.

Furthermore, the colored part C of the root canal sealer P according to the invention is formed over a uniform length and a limit of length (approximately 3 mm) exposed in the front of the dental instrument body 10 as shown in FIGS. 1 and 2. Since the range to be utilized while using each root canal sealer P is no more than about 16 mm from the front end of each root canal sealer, no problem is posed in using the coloring part C for coloring the head P' of the root canal sealer P directly.

The front end of the pincers, etc. may be put in through the vertical groove 13 formed in the rear of the dental instrument body 10. Hence the root canal sealer concerned may be taken out or put in easily if the coloring is wrong or products are made poorly.

Figure 7:
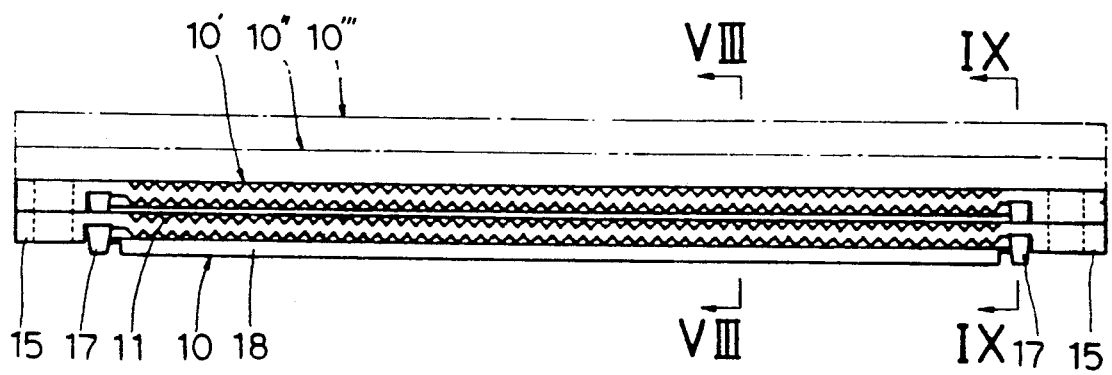
FIG. 7 is an elevation view showing a state that a number of dental instruments according to the invention are laminated.
Figure 8:
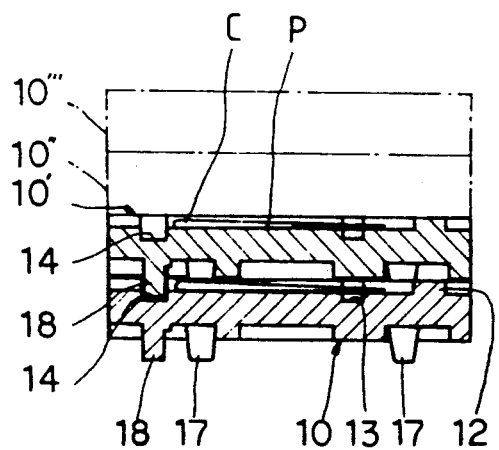
FIG. 8 is a sectional view taken on the line VIII—VIII in FIG. 7.
Figure 9:
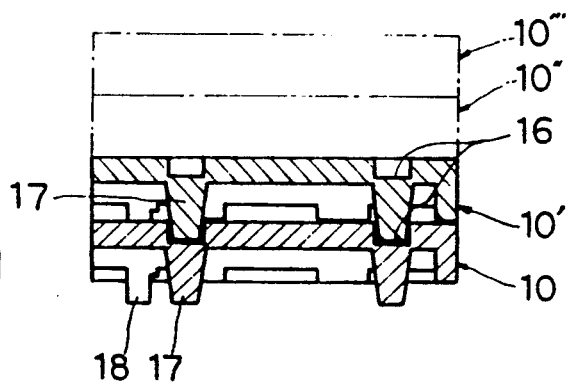
FIG. 9 is a sectional view taken on the line IX—IX in FIG. 7.

FIGS. 7 and 9 show conditions for maintaining thus colored and dried root canal sealers P before they are put by dimension in a packing box or vessel. For safekeeping of such sealers, the front side of the body 10 is lifted slightly to cover a pressing plate 20 mounted on the upper face of the dental instrument body 10. This is done such that the colored head P' of each root canal sealer P is pushed into each concave groove 11, and the pressing plate 20 of its upper part is separated to make each root canal sealer P lie on the inside of the vertical groove 14 formed in the front of the dental instrument body 10. Then each insert projection 17 and vertical projection is formed on the bottom of the upper dental instrument body 10', 10" and 10''' are engaged with each insert groove 16 and vertical groove 14 of its lower dental instrument body 10, 10' and 10" by continuously laminating the second and third dental instrument body 10', 10", 10''' on the upper part of the dental instrument body 10, so that a number of dental instrumental bodies 10 containing a given number of root canal sealers P may be kept simply and stably.

As described above, making the dimension of root canal sealer and cleaner easily visible with naked eye involves coloring the head of each dental root canal sealer and cleaner having a slight difference in size with a prescribed hue. The invention makes the head of each root canal sealer and cleaner to be colored through a simple coloring process using a dental instrument body of a simple structure in which a certain number of root canal sealers and cleaners can be arranged and contained, and a pressing plate covered on the upper part of the dental instrument body. At the same time it makes each root canal sealer and cleaner safely. The invention has the effect of allowing a colored part having a uniform length to be formed more easily at the head of each root canal sealer and cleaner. The quantity of such root canal sealers and cleaners can be calculated exactly, and lots of root canal sealers and cleaners can be handled and managed simply and safely.

What is claimed is:

1. A dental root canal sealer for filling and sealing a root canal and having a discriminating part, said sealer comprising a body in a substantially needle form the front end of which is thin and the opposite end of which includes a slightly convex head, a dimension discriminating part for indicating a dimension, said dimension discriminating part being provided on the surface of the head of said body and colored in a selected hue.

2. A sealer as in claim 1, wherein the color of said dimension discriminating part is produced by soaking the sealer body at the dimension discriminating part in a coloring medium.

* * * * *